(12) United States Patent
Ferri

(10) Patent No.: US 10,842,635 B2
(45) Date of Patent: Nov. 24, 2020

(54) TEMPORO-MANDIBULAR PROSTHESIS

(71) Applicants: Institut National De La Sante Et De La Recherche Medicale (INSERM), Paris (FR); Centre Hospitalier Regional Universitaire De Lille, Lille (FR); Universite De Lille, Lille (FR)

(72) Inventor: Joel Ferri, Lille (FR)

(73) Assignees: Institut National De La Sante Et De La Recherche Medicale (INSERM), Paris (FR); Centre Hospitalier Regional Universitaire De Lille, Lille (FR); Universite De Lille, Lille (FR)

( * ) Notice: Subject to any disclaimer, the term of this patent is extended or adjusted under 35 U.S.C. 154(b) by 0 days.

(21) Appl. No.: 16/486,594

(22) PCT Filed: Feb. 14, 2018

(86) PCT No.: PCT/EP2018/053619
§ 371 (c)(1),
(2) Date: Aug. 16, 2019

(87) PCT Pub. No.: WO2018/149849
PCT Pub. Date: Aug. 23, 2018

(65) Prior Publication Data
US 2020/0008945 A1 Jan. 9, 2020

(30) Foreign Application Priority Data
Feb. 17, 2017 (EP) .................................. 17305178

(51) Int. Cl.
*A61F 2/30* (2006.01)

(52) U.S. Cl.
CPC .. *A61F 2/3099* (2013.01); *A61F 2002/30329* (2013.01); *A61F 2002/30991* (2013.01);
(Continued)

(58) Field of Classification Search
CPC .......... A61F 2/3099; A61F 2002/30991; A61F 2002/30993; A61F 2002/30383; A61F 2002/30401
See application file for complete search history.

(56) References Cited

U.S. PATENT DOCUMENTS

| 5,549,680 A | * | 8/1996 | Gordon | ................. A61F 2/3099 623/17.17 |
| 6,132,466 A | * | 10/2000 | Hoffman | ............... A61F 2/3099 623/17.17 |

(Continued)

FOREIGN PATENT DOCUMENTS

| CN | 104546225 A | 4/2015 |
| EP | 0628293 A1 | 12/1994 |

OTHER PUBLICATIONS

International Search Report (ISR) for PCT/EP2018/053619 dated Apr. 30, 2018 (4 pages).
(Continued)

*Primary Examiner* — Brian A Dukert
(74) *Attorney, Agent, or Firm* — Shumaker, Loop & Kendrick, LLP

(57) ABSTRACT

A temporo-mandibular prosthesis including a glenoid part and a condylar part intended to be articulated relative to the glenoid part. The glenoid part including a glenoid support made in a metallic material; and a glenoid insert made in a non-metal lie material, and defining a seat for a head of said condylar part to define said articulation, wherein the glenoid support defines a housing having an opening through which said glenoid insert is insertable into said housing, said opening opening on an external side (E) of said glenoid support, the glenoid support comprising a tab configurable in a passive position and in an active position in which said tab allows and forbids, respectively, the insertion and the
(Continued)

extraction, respectively, of said glenoid insert into and out of said housing, respectively.

14 Claims, 1 Drawing Sheet

(52) U.S. Cl.
CPC .............. *A61F 2002/30993* (2013.01); *A61F 2220/0041* (2013.01); *A61F 2250/006* (2013.01); *A61F 2310/00023* (2013.01)

(56) References Cited

U.S. PATENT DOCUMENTS

| | | |
|---|---|---|
| 2011/0137422 A1 | 6/2011 | Wilkes |
| 2015/0320567 A1* | 11/2015 | Terrill .................. A61F 2/4202 623/21.18 |

OTHER PUBLICATIONS

Written Opinion (WO) for PCT/EP2018/053619 dated Apr. 30, 2018 (5 pages).
International Search Report for PCT/EP2018/053619 dated Apr. 30, 2018 (4 pages).

* cited by examiner

TEMPORO-MANDIBULAR PROSTHESIS

TECHNICAL FILED

The invention concerns a temporo-mandibular prosthesis, as well as a method for assembling such prosthesis.

BACKGROUND

A temporo-mandibular prosthesis or «temporo-mandibular joint (TMJ)» conventionally comprises a glenoid part and a condylar part articulated on the glenoid part. In the service position, the glenoid part is rigidly fixed to a temporal bone, and the condylar part is rigidly fixed on a mandible of the patient.

To avoid any release of metallic particles in the patient, a metal-metal contact between the glenoid part and the condylar part should be avoided. However, it is advantageous that the glenoid part be in metal for an efficient and compact fixation to the temporal bone.

Moreover, the glenoid and mandibular parts must be very precisely fixed on the temporal bone and the mandible, respectively, to guarantee an efficient articulation. There is a need for solutions which answer, at least partially, to these constraints. The aim of the present invention is to provide such a solution.

SUMMARY OF THE INVENTION

To this end, the invention provides a temporo-mandibular prosthesis.

As it will be described in further details, using a non-metallic material, and in particular a polymeric material for the glenoid insert avoids any release of metallic particles due to the friction between the glenoid part and the condylar part.

In addition, the glenoid insert can be fixed on the glenoid support only once the glenoid support has been fixed on the temporal bone and the condylar part has been fixed on the mandible. It is therefore possible choosing a glenoid insert which is perfectly fitting the condylar part in the service position.

Finally, the glenoid insert can be easily immobilized with respect to the glenoid support by a simple change of the position of the tab. This makes the definitive fixation of the glenoid insert easier.

Preferably, prosthesis according to the present invention comprises one or several optional characteristics of the temporo-mandibular prostheses disclosed herein.

The invention also concerns a method for assembling a prosthesis. Preferably, a method according to the present invention comprises one or several optional characteristics of the temporo-mandibular prosthesis/prostheses disclosed herein.

The invention also concerns a temporo-mandibular prosthesis comprising a glenoid part and a condylar part intended to be articulated relative to the glenoid part in a service position in which said glenoid part and condylar part are rigidly fixed to a temporal bone and a mandible of a patient, respectively, said condylar part comprising a first stop configured to bear on the neck of a mandible of the patient, and a second stop configured to bear on the ramus of said mandible.

Advantageously, the condylar part can be easily arranged relative to the mandible with a very high precision. The operator only puts the first stop on the neck of the mandible and then rotates the condylar part in an antero-posterior movement, until the second stop abuts the ramus of the mandible.

BRIEF DESCRIPTION OF THE DRAWING

The invention will be better understood from the reading of the detailed description that follows, with reference to an exemplary and non-limiting embodiment thereof, and by the examination of the appended drawing, in which.

DEFINITIONS

Figure 1:
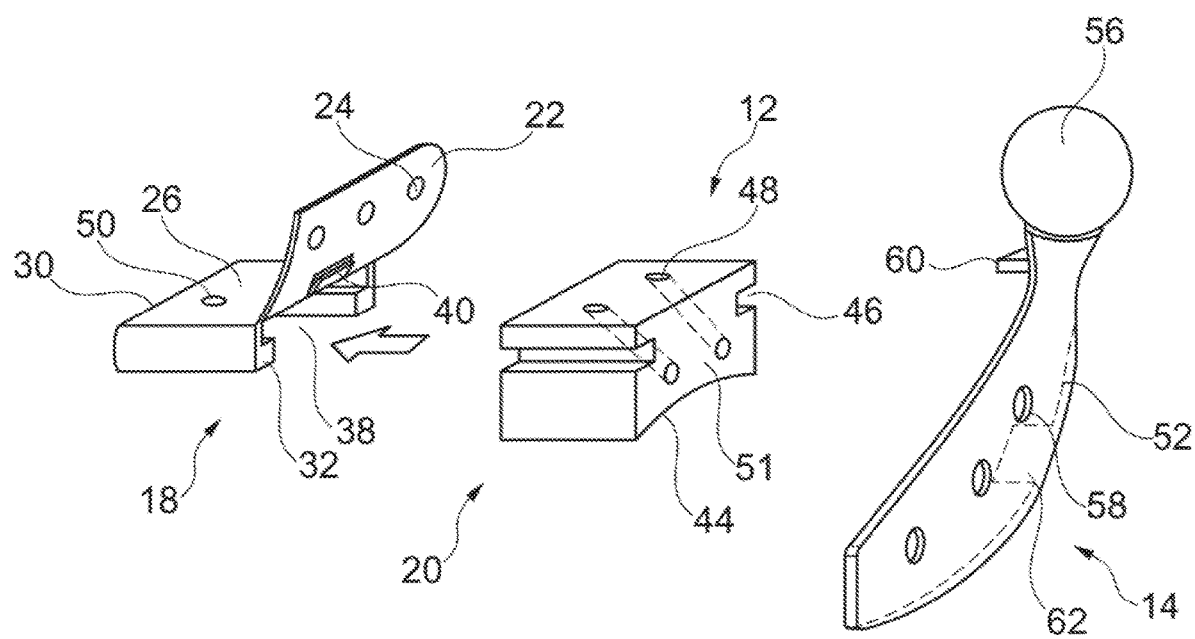
FIG. 1 represents a prosthesis according to the invention in a disassembled position.

A «patient» is a living being, and in particular a human being, receiving a prosthesis according to the invention.

«Comprise» should be understood in its broad and non limitative meaning, unless it is otherwise provided.

DETAILED DESCRIPTION OF A PREFERRED EMBODIMENT

The figures represent prosthesis 10 comprising a glenoid part 12 and a condylar part 14.

The glenoid part 12 comprises a glenoid support 18 and a glenoid insert 20.

The glenoid support 18 is made of a metallic material and, preferably, is made in titanium or in a titanium alloy.

The glenoid support 18 comprises a support anchoring plate 22 which is intended to be fixed to a temporal bone. Preferably, the support anchoring plate comprises glenoid anchoring holes 24 through which glenoid anchoring screws can be driven into the temporal bone.

In a preferred embodiment, the support anchoring plate is a grid, which makes the regrowth of the bone and the cells colonization faster.

The glenoid support 18 comprises a housing 26 configured to receive the glenoid insert 20.

More precisely, the housing 26 comprises an opening 28 through which the glenoid insert 20 can be introduced into the housing 26.

Opposite to the opening 28, the housing 26 comprises a bottom 30.

The housing 26 also comprises two guiding rails 32 on which the glenoid insert can slide, just as a drawer may slide in a dresser.

The housing 26 opens on the external side of the glenoid support 18, i.e. opens towards the cheeks, the bottom 30 being oriented toward the medial part of cranial base, i.e. the internal side. On FIG. 2, the external and internal sides are referred to as «E» and «I», respectively. This arrangement makes the insertion of the glenoid insert 20 into the housing 26 much easier.

Preferably, the external side E is the side of the glenoid support on which the support anchoring plate 22 extends.

Figure 2:
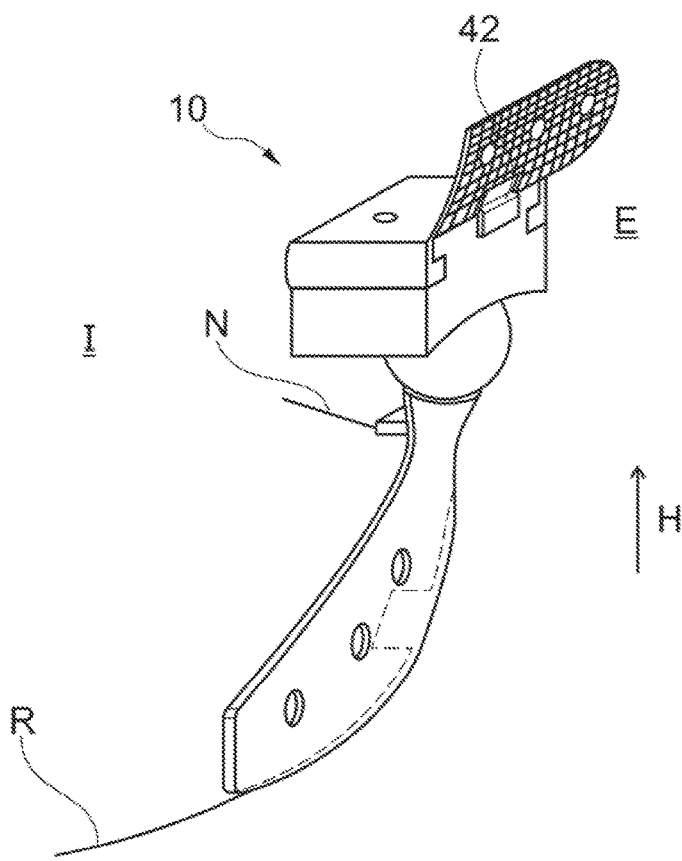
FIG. 2 represents the same prosthesis in an assembled position.

According to the invention, the glenoid support 18 also comprises a tab 40 which is plastically deformable between passive and active positions, as represented in FIGS. 1 and 2, respectively. The tab 40 therefore keeps its shape in the passive and active positions.

In the passive position (FIG. 1), the tab 40 does not hinder the introduction of the glenoid insert 20 into the housing 26, nor its extraction out of the housing.

In the active position (FIG. 2), the tab 40 hinders the introduction of the glenoid insert 20 into the housing or, in the service position as represented in FIG. 2, its extraction out of said housing. Preferably, when the glenoid insert is inserted in the housing 26, the tab maintains in the active position, the glenoid insert 20 in contact with the bottom 30 of the housing.

In a preferred embodiment, the tab is configured to be manually deformable from the passive position to the active position, preferably without any tool.

In an embodiment, the tab 40 is integrally formed with the support anchoring plate 22, preferably along with the housing 26.

To make the bending of the tab 40 easier, a weakening line 42 is preferably provided. The weakening line may be formed by a local reduction of thickness and/or by the provision of holes.

The glenoid insert 20 is preferably made in a polymeric material, preferably in polyethylene. It defines a bearing surface 44 intended to receive the head 56 of the condylar part 14. The bearing surface 44 is preferably concave, preferably substantially spherical.

The glenoid insert 20 also comprises two lateral grooves 46 configured to cooperate with the guiding rails 32 of the glenoid part 18.

Finally, the glenoid insert 20 comprises insert screw holes 48 which, when the glenoid inserted is in contact with the bottom 30 of the housing 26, are facing corresponding support screw holes 50. In the service position, assembling screws cross the glenoid insert 20, through the insert screw holes 48, the glenoid support 18, through the support screw holes 50, and, preferably penetrate into the temporal bone. Preferably, the insert screw holes 48 open on the external face 51 of the insert, i.e. on the face which, in the service position, faces the skin.

The condylar part 14 comprises a condylar anchoring plate 52 supporting a head 56 intended to bear on the bearing surface 44. The condylar anchoring plate 52 comprises condylar anchoring holes 58 so as to fix the condylar anchoring plate 52 to the mandible, with condylar anchoring screws.

The condylar anchoring plate 22 also comprises first and second stops 60 and 62. Advantageously, the stops 60 and 62 make the positioning of the condylar part on the mandible much easier.

In the represented embodiment, the second stop 62 is obtained by the bending of the condylar anchoring plate 52, preferably toward the inside of the mouth. The first stop is welded on the condylar anchoring plate 52.

The assembling of the different parts of a prosthesis according to the invention is preferably as follows:

The glenoid anchoring plate 52 and the condylar anchoring plate 52 are fixed to the temporal bone and the mandible of a patient, respectively, with glenoid and condylar anchoring screws crossing the glenoid anchoring holes 24 and the condylar anchoring holes 58, respectively.

The stops 60 and 62 help finding the right position on the mandible before the fixing of the condylar part 14 on the mandible. More precisely, the operator first puts the first stop 60 on the neck N of the mandible which has been severed. This defines the position of the condylar part 14 along the height direction H. Then the operator rotates the condylar part 14 in an antero-posterior movement, until the second stop 62 abuts the ramus R of the mandible.

The operator then pushes the glenoid insert 20 so as to engage the two rails 32 inside the two grooves 46, respectively. Then, the operator pushes the glenoid insert 20 on the rails 32, toward the bottom 30, preferably until the glenoid insert 20 abuts said bottom 30.

Advantageously, the opening of the housing 26 toward the external side E makes the insertion of the glenoid insert 20 easy.

The operator then bends the tab 40 from its passive position (FIG. 1) to its active position (FIG. 2), wherein the tab 40 at least partially extends across the opening 28 of the housing 26. The tab 40, in its active position (FIG. 2), bears on the glenoid insert 20, which is therefore maintained fixed between the bottom 30 and the tab 40. Laterally, the glenoid insert is maintained by the cooperation of the guiding rails 32 with the grooves 46. With the tab 40, the operator therefore immobilizes the glenoid insert 20 relative to the glenoid support 18.

The operator then tests whether the cooperation between the head 56 of the condylar part with the bearing surface 44 of the glenoid insert 20 is perfectly correct.

If it is not the case, the operator can bend the tab 40 in the opposite direction, until its passive position. The operator can then extract the glenoid insert and adapt it, i.e. modify or change it, so that it better matches with the head 56 of the condylar part 14.

Advantageously, the operator can easily test different glenoid inserts 20, without definitely fixing any insert part on the glenoid support 18.

Consequently, the operator can find a glenoid insert 20 which perfectly matches with the condylar part 14.

Once the operator has found the right glenoid insert 20, he drives assembling screws across insert screw holes 48 and support screw holes 50, and, preferably, inside the temporal bone. The definitive fixation of the glenoid insert 20, with said assembling screws, is made easier by the immobilization of the glenoid insert 20 with the tab 40.

Finally, since the glenoid insert 20, which cooperates with the condylar part 14, is in a non-metallic, preferably in a polymeric material, there is no metal-metal friction, which advantageously avoids any release of metallic particles in the mouth of the patient.

As it is clear now, the invention provides a prosthesis which can be easily tested until it perfectly fits the patient's needs, and which, in use, does not incur any release of metallic particles.

Of course, the invention is not limited to the embodiment which was disclosed and represented, only provided as an illustrative and non-limitative example.

The invention claimed is:

1. A temporo-mandibular prosthesis comprising a glenoid part and a condylar part configured to be articulated relative to the glenoid part in a service position in which said glenoid part and condylar part are configured to be rigidly fixed to a temporal bone and a mandible of a patient, respectively, said glenoid part comprising:
　　a glenoid support made in a metallic material; and
　　a glenoid insert made in a non-metallic material, and defining a seat for a head of said condylar part to define said articulation,
　　wherein the glenoid support defines a housing having an opening through which said glenoid insert is insertable into said housing, said opening on an external side of said glenoid support, the external side being the side of said glenoid support which is oriented towards the skin of the patient in the service position,
　　the glenoid support comprising a tab configurable in a passive position and in an active position in which said tab allows and forbids, respectively, the insertion and the extraction, respectively, of said glenoid insert into and out of said housing, respectively, said tab being plastically deformable between said passive and active positions.

2. The prosthesis according to claim 1, wherein the glenoid support comprises sliding guides configured to guide a sliding of said glenoid insert into and out of said housing, in the passive position of said tab.

3. The prosthesis according to claim 2, wherein said sliding guides are rails.

4. The prosthesis according to claim 1, wherein said glenoid support comprises a bottom limiting the insertion of the glenoid insert into said housing.

5. The prosthesis according to claim 1, wherein the glenoid insert comprises an insert screw hole and the glenoid support comprises a support screw hole, said insert screw hole and support screw holes being configured so that, when the glenoid insert is in the housing and in contact with said bottom, an assembling screw may cross said insert screw hole and said support screw hole to assemble the glenoid insert and the glenoid support.

6. The prosthesis according to claim 5, wherein said insert screw hole opens on a face of the insert which, in the service position, faces the skin of the patient.

7. The prosthesis according to claim 1, wherein said tab is manually deformable.

8. The prosthesis according to claim 1, wherein the tab at least partially closes said opening in the active position.

9. The prosthesis according to claim 1, wherein the glenoid support comprises a grid configured to be in contact with the temporal bone in the service position.

10. The prosthesis according to claim 1, wherein the glenoid support is in titanium or in a titanium alloy and/or the glenoid insert is in polyethylene.

11. The prosthesis according to claim 1, wherein the condylar part comprises a first stop configured to bear on the neck of a mandible of the patient, and/or a second stop configured to bear on the ramus of said mandible.

12. A method for assembling the prosthesis of claim 1, said method comprising the following steps:

a) inserting the glenoid insert into the housing until the glenoid insert abuts on a bottom of the housing, the tab being in the passive position;

b) putting the tab in the active position, so as to immobilize the glenoid insert relative to said housing.

13. The method according to claim 12, further comprising, after step b), the following steps:

c) test whether the condylar part matches the glenoid insert;

d) if not, put the tab in a passive position, extract the glenoid insert out of the housing, adapt the glenoid insert so that it better matches the condylar part, insert the adapted glenoid insert into the housing, put the tab in an active position, and restart step c), e) rigidly fix the glenoid insert on the glenoid support.

14. The prosthesis according to claim 1, wherein said glenoid support comprises a support anchoring plate intended to be fixed to a temporal bone, and the tab is integrally formed with the support anchoring plate.

* * * * *